(12) United States Patent
McCabe

(10) Patent No.: US 7,780,052 B2
(45) Date of Patent: Aug. 24, 2010

(54) TRIM REMOVAL SYSTEM

(75) Inventor: John A. McCabe, Sheboygan Falls, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 986 days.

(21) Appl. No.: 11/436,274

(22) Filed: May 18, 2006

(65) Prior Publication Data

US 2007/0267149 A1   Nov. 22, 2007

(51) Int. Cl.
  *B26F 3/00* (2006.01)
  *B29C 63/00* (2006.01)
  *B29C 65/00* (2006.01)

(52) U.S. Cl. .................................. 225/100; 156/510

(58) Field of Classification Search .................. None
  See application file for complete search history.

(56) References Cited

U.S. PATENT DOCUMENTS

| 135,145 | A | 1/1873 | Murphy |
|---|---|---|---|
| 293,353 | A | 2/1884 | Purvis |
| 312,257 | A | 2/1885 | Cotton et al. |
| 410,123 | A | 8/1889 | Stilwell |
| 432,742 | A | 7/1890 | Stanley |
| 643,821 | A | 2/1900 | Howlett |
| 1,393,524 | A | 10/1921 | Grupe |
| 1,605,842 | A | 11/1926 | Jones |
| 1,686,595 | A | 10/1928 | Belluche |
| 1,957,651 | A | 5/1934 | Joa |
| 2,009,857 | A | 7/1935 | Potdevin |
| 2,054,832 | A | 9/1936 | Potdevin |
| 2,117,432 | A | 5/1938 | Linscott |
| 2,128,746 | A | 8/1938 | Joa |
| 2,131,808 | A | 10/1938 | Joa |
| 2,164,408 | A | 7/1939 | Joa |
| 2,167,179 | A | 7/1939 | Joa |
| 2,171,741 | A | 9/1939 | Cohn et al. |
| 2,213,431 | A | 9/1940 | Joa |
| 2,254,290 | A | 9/1941 | Joa |
| 2,254,291 | A | 9/1941 | Joa |
| 2,282,477 | A | 5/1942 | Joa |
| 2,286,096 | A | 6/1942 | Joa |
| 2,296,931 | A | 9/1942 | Joa |
| 2,304,571 | A | 12/1942 | Joa |
| 2,324,930 | A | 7/1943 | Joa |
| 2,345,937 | A | 4/1944 | Joa |

(Continued)

FOREIGN PATENT DOCUMENTS

BE   1007854   11/1995

(Continued)

*Primary Examiner*—Mark A Osele
*Assistant Examiner*—Nickolas Harm
(74) *Attorney, Agent, or Firm*—Ryan, Kromholz & Manion, S.C.

(57) ABSTRACT

A system for removing chips from a web is disclosed, the system having a rotationally variable speed shoe for receiving a chip, a rotationally constant speed transfer roll for receiving a portion of a web from a die and anvil system, with the shoe initially rotating at a constant speed, slowing to allow a portion of the web to rip away from the chip at a leading rotational edge of the chip, next increasing in rotational speed to allow the chip to rip away from the web at a trailing rotational edge of the chip.

13 Claims, 5 Drawing Sheets

U.S. PATENT DOCUMENTS

| | | |
|---|---|---|
| 2,466,240 A | 4/1949 | Joa |
| 2,481,929 A | 9/1949 | Joa |
| 2,510,229 A | 6/1950 | Joa |
| 2,540,844 A | 2/1951 | Strauss |
| 2,584,002 A | 1/1952 | Elser et al. |
| 2,591,359 A | 4/1952 | Joa |
| 2,618,816 A | 11/1952 | Joa |
| 2,702,406 A | 2/1955 | Reed |
| 2,721,554 A | 10/1955 | Joa |
| 2,730,144 A | 1/1956 | Joa |
| 2,772,611 A | 12/1956 | Heywood |
| 2,780,253 A | 2/1957 | Joa |
| 2,785,609 A | 3/1957 | Billeb |
| 2,811,905 A | 11/1957 | Kennedy, Jr. |
| 2,839,059 A | 6/1958 | Joa |
| 2,842,169 A | 7/1958 | Joa |
| 2,851,934 A | 9/1958 | Heywood |
| 2,875,724 A | 3/1959 | Joa |
| 2,913,862 A | 11/1959 | Sabee |
| 2,939,461 A | 6/1960 | Joa |
| 2,960,143 A | 11/1960 | Joa |
| 2,990,081 A | 6/1961 | Neui et al. |
| 2,991,739 A | 7/1961 | Joa |
| 3,016,207 A | 1/1962 | Comstock |
| 3,016,582 A | 1/1962 | Joa |
| 3,017,795 A | 1/1962 | Joa |
| 3,020,687 A | 2/1962 | Joa |
| 3,021,135 A | 2/1962 | Joa |
| 3,024,957 A | 3/1962 | Pinto |
| 3,053,427 A | 9/1962 | Wasserman |
| 3,054,516 A | 9/1962 | Joa |
| 3,069,982 A | 12/1962 | Heywood et al. |
| 3,086,253 A | 4/1963 | Joa |
| 3,087,689 A | 4/1963 | Heim |
| 3,091,408 A | 5/1963 | Schoeneman |
| 3,114,994 A | 12/1963 | Joa |
| 3,122,293 A | 2/1964 | Joa |
| 3,128,206 A | 4/1964 | Dungler |
| 3,203,419 A | 8/1965 | Joa |
| 3,230,955 A | 1/1966 | Joa et al. |
| 3,268,954 A | 8/1966 | Joa |
| 3,288,037 A | 11/1966 | Burnett |
| 3,289,254 A | 12/1966 | Joa |
| 3,291,131 A | 12/1966 | Joa |
| 3,301,114 A | 1/1967 | Joa |
| 3,322,589 A | 5/1967 | Joa |
| 3,342,184 A | 9/1967 | Joa |
| 3,356,092 A | 12/1967 | Joa |
| 3,360,103 A | 12/1967 | Johnson |
| 3,363,847 A | 1/1968 | Joa |
| 3,391,777 A | 7/1968 | Joa |
| 3,454,442 A | 7/1969 | Heller, Jr. |
| 3,470,848 A | 10/1969 | Dreher |
| 3,484,275 A | 12/1969 | Lewicki, Jr. |
| 3,502,322 A | 3/1970 | Cran |
| 3,521,639 A | 7/1970 | Joa |
| 3,526,563 A | 9/1970 | Schott, Jr. |
| 3,538,551 A | 11/1970 | Joa |
| 3,540,641 A | 11/1970 | Besnyo et al. |
| 3,575,170 A | 4/1971 | Clark |
| 3,607,578 A | 9/1971 | Berg et al. |
| 3,635,462 A | 1/1972 | Joa |
| 3,656,741 A | 4/1972 | Macke et al. |
| 3,666,611 A | 5/1972 | Joa |
| 3,673,021 A | 6/1972 | Joa |
| 3,685,818 A | 8/1972 | Burger |
| 3,728,191 A | 4/1973 | Wierzba et al. |
| 3,751,224 A | 8/1973 | Wackerle |
| 3,772,120 A | 11/1973 | Radzins |
| 3,796,360 A | 3/1974 | Alexeff |
| 3,816,210 A | 6/1974 | Aoko et al. |
| 3,847,710 A | 11/1974 | Blomqvist et al. |
| 3,854,917 A | 12/1974 | McKinney et al. |
| 3,883,389 A | 5/1975 | Schott, Jr. |
| 3,888,400 A | 6/1975 | Wiig |
| 3,903,768 A | 9/1975 | Amberg et al. |
| 3,904,147 A | 9/1975 | Taitel et al. |
| 3,918,698 A | 11/1975 | Coast |
| 3,960,646 A | 6/1976 | Wiedamann |
| 3,991,994 A | 11/1976 | Farish |
| 4,002,005 A | 1/1977 | Mueller et al. |
| 4,003,298 A | 1/1977 | Schott, Jr. |
| 4,009,814 A | 3/1977 | Singh |
| 4,009,815 A | 3/1977 | Ericson et al. |
| 4,053,150 A | 10/1977 | Lane |
| 4,056,919 A | 11/1977 | Hirsch |
| 4,081,301 A | 3/1978 | Buell |
| 4,090,516 A | 5/1978 | Schaar |
| 4,094,319 A | 6/1978 | Joa |
| 4,103,595 A | 8/1978 | Corse |
| 4,106,974 A | 8/1978 | Hirsch |
| 4,108,584 A | 8/1978 | Radzins et al. |
| 4,136,535 A | 1/1979 | Audas |
| 4,141,193 A | 2/1979 | Joa |
| 4,141,509 A | 2/1979 | Radzins |
| 4,142,626 A | 3/1979 | Bradley |
| 4,157,934 A | 6/1979 | Ryan et al. |
| 4,165,666 A | 8/1979 | Johnson et al. |
| 4,168,776 A | 9/1979 | Hoeboer |
| 4,171,239 A | 10/1979 | Hirsch et al. |
| 4,205,679 A | 6/1980 | Repke et al. |
| 4,208,230 A | 6/1980 | Magarian |
| 4,213,356 A | 7/1980 | Armitage |
| 4,215,827 A | 8/1980 | Roberts et al. |
| 4,222,533 A | 9/1980 | Pongracz |
| 4,223,822 A | 9/1980 | Clitheroe |
| 4,231,129 A | 11/1980 | Winch |
| 4,236,955 A | 12/1980 | Prittie |
| 4,275,510 A | 6/1981 | George |
| 4,284,454 A | 8/1981 | Joa |
| 4,307,800 A | 12/1981 | Joa |
| 4,316,756 A | 2/1982 | Wilson |
| 4,342,206 A | 8/1982 | Rommel |
| 4,364,787 A | 12/1982 | Radzins |
| 4,374,576 A | 2/1983 | Ryan |
| 4,379,008 A | 4/1983 | Gross et al. |
| 4,394,898 A | 7/1983 | Campbell |
| 4,411,721 A | 10/1983 | Wishart |
| 4,452,597 A | 6/1984 | Achelpohl |
| 4,492,608 A | 1/1985 | Hirsch et al. |
| 4,501,098 A | 2/1985 | Gregory |
| 4,508,528 A | 4/1985 | Hirsch et al. |
| 4,522,853 A | 6/1985 | Szonn et al. |
| 4,551,191 A | 11/1985 | Kock et al. |
| 4,586,199 A | 5/1986 | Birring |
| 4,589,945 A | 5/1986 | Polit |
| 4,603,800 A | 8/1986 | Focke et al. |
| 4,614,076 A | 9/1986 | Rathemacher |
| 4,619,357 A | 10/1986 | Radzins et al. |
| 4,634,482 A | 1/1987 | Lammers |
| 4,641,381 A | 2/1987 | Heran et al. |
| 4,642,150 A | 2/1987 | Stemmler |
| 4,642,839 A | 2/1987 | Urban |
| 4,650,530 A | 3/1987 | Mahoney et al. |
| 4,663,220 A | 5/1987 | Wisnecki et al. |
| 4,672,705 A | 6/1987 | Bors et al. |
| 4,675,062 A | 6/1987 | Instance |
| 4,693,056 A | 9/1987 | Raszewski |
| 4,701,239 A | 10/1987 | Craig |
| 4,726,874 A | 2/1988 | Van Vilet |
| 4,726,876 A | 2/1988 | Tomsovic et al. |
| 4,743,241 A | 5/1988 | Igaue et al. |
| 4,751,997 A | 6/1988 | Hirsch |
| 4,753,429 A | 6/1988 | Irvine et al. |

| | | | | | |
|---|---|---|---|---|---|
| 4,756,141 A | 7/1988 | Hirsch et al. | 5,556,360 A | 9/1996 | Kober et al. |
| 4,764,325 A | 8/1988 | Angstadt | 5,556,504 A | 9/1996 | Rajala et al. |
| 4,765,780 A | 8/1988 | Angstadt | 5,560,793 A | 10/1996 | Ruscher et al. |
| 4,776,920 A | 10/1988 | Ryan | 5,602,747 A | 2/1997 | Rajala |
| 4,777,513 A | 10/1988 | Nelson | 5,624,420 A | 4/1997 | Bridges et al. |
| 4,782,647 A | 11/1988 | Williams et al. | 5,624,428 A | 4/1997 | Sauer |
| 4,785,986 A | 11/1988 | Daane et al. | 5,628,738 A | 5/1997 | Suekane |
| 4,795,510 A | 1/1989 | Wittrock et al. | 5,634,917 A | 6/1997 | Fujioka et al. |
| 4,801,345 A | 1/1989 | Dussaud et al. | 5,643,165 A | 7/1997 | Klekamp |
| 4,802,570 A | 2/1989 | Hirsch et al. | 5,643,396 A | 7/1997 | Rajala et al. |
| 4,840,609 A | 6/1989 | Jones et al. | 5,645,543 A | 7/1997 | Nomura et al. |
| 4,845,964 A | 7/1989 | Bors et al. | 5,659,229 A | 8/1997 | Rajala |
| 4,864,802 A | 9/1989 | D'Angelo | 5,660,657 A | 8/1997 | Rajala et al. |
| 4,878,985 A * | 11/1989 | Thomsen et al. ............ 156/459 | 5,660,665 A | 8/1997 | Jalonen |
| 4,880,102 A | 11/1989 | Indrebo | 5,683,376 A | 11/1997 | Kato et al. |
| 4,888,231 A | 12/1989 | Angstadt | RE35,687 E | 12/1997 | Igaue et al. |
| 4,892,536 A | 1/1990 | Des Marais et al. | 5,693,165 A | 12/1997 | Schmitz |
| 4,904,440 A | 2/1990 | Angstadt | 5,699,653 A | 12/1997 | Hartman et al. |
| 4,908,175 A | 3/1990 | Angstadt | 5,707,470 A | 1/1998 | Rajala et al. |
| 4,909,019 A | 3/1990 | Delacretaz et al. | 5,711,832 A | 1/1998 | Glaug et al. |
| 4,925,520 A | 5/1990 | Beaudoin et al. | 5,725,518 A | 3/1998 | Coates |
| 4,927,322 A | 5/1990 | Schweizer et al. | 5,745,922 A | 5/1998 | Rajala et al. |
| 4,927,582 A | 5/1990 | Bryson | 5,746,869 A | 5/1998 | Hayden et al. |
| 4,937,887 A | 7/1990 | Schreiner | 5,749,989 A | 5/1998 | Linman et al. |
| 4,963,072 A | 10/1990 | Miley et al. | 5,788,797 A | 8/1998 | Herrin et al. |
| 4,987,940 A | 1/1991 | Straub et al. | 5,817,199 A | 10/1998 | Brennecke et al. |
| 4,994,010 A | 2/1991 | Doderer-Winkler | 5,829,164 A | 11/1998 | Kotitschke |
| 5,000,806 A | 3/1991 | Merkatoris et al. | 5,836,931 A | 11/1998 | Toyoda et al. |
| 5,021,111 A | 6/1991 | Swenson | 5,858,012 A | 1/1999 | Yamaki et al. |
| 5,025,910 A | 6/1991 | Lasure et al. | 5,865,393 A | 2/1999 | Kreft et al. |
| 5,045,039 A | 9/1991 | Bay | 5,868,727 A | 2/1999 | Barr et al. |
| 5,062,597 A | 11/1991 | Martin et al. | 5,876,027 A | 3/1999 | Fukui et al. |
| 5,064,179 A | 11/1991 | Martin et al. | 5,876,792 A | 3/1999 | Caldwell |
| 5,080,741 A | 1/1992 | Nomura et al. | 5,879,500 A | 3/1999 | Herrin et al. |
| 5,094,658 A | 3/1992 | Smithe et al. | 5,902,431 A | 5/1999 | Wilkinson et al. |
| 5,096,532 A | 3/1992 | Neuwirth et al. | 5,932,039 A | 8/1999 | Popp et al. |
| 5,108,017 A | 4/1992 | Adamski et al. | 5,938,193 A | 8/1999 | Bluemle et al. |
| 5,109,767 A | 5/1992 | Nyfeler et al. | 5,964,970 A | 10/1999 | Woolwine et al. |
| 5,110,403 A | 5/1992 | Ehlert | 6,036,805 A | 3/2000 | McNichols |
| 5,127,981 A | 7/1992 | Straub et al. | 6,043,836 A | 3/2000 | Kerr et al. |
| 5,131,525 A | 7/1992 | Musschoot | 6,050,517 A | 4/2000 | Dobrescu et al. |
| 5,147,487 A | 9/1992 | Nomura et al. | 6,074,110 A | 6/2000 | Verlinden et al. |
| 5,163,594 A | 11/1992 | Meyer | 6,076,442 A | 6/2000 | Arterburn et al. |
| 5,171,239 A | 12/1992 | Igaue et al. | 6,098,249 A | 8/2000 | Toney et al. |
| 5,176,244 A | 1/1993 | Radzins et al. | 6,123,792 A | 9/2000 | Samida et al. |
| 5,183,252 A | 2/1993 | Wolber et al. | 6,171,432 B1 | 1/2001 | Brisebois et al. |
| 5,188,627 A | 2/1993 | Igaue et al. | 6,183,576 B1 | 2/2001 | Couillard et al. |
| 5,195,684 A | 3/1993 | Radzins | 6,210,386 B1 | 4/2001 | Inoue |
| 5,203,043 A | 4/1993 | Riedel | 6,212,859 B1 | 4/2001 | Bielik, Jr. et al. |
| 5,213,645 A | 5/1993 | Nomura et al. | 6,250,048 B1 | 6/2001 | Linkiewicz |
| 5,223,069 A | 6/1993 | Tokuno et al. | 6,264,784 B1 | 7/2001 | Menard et al. |
| 5,226,992 A | 7/1993 | Morman | 6,276,421 B1 | 8/2001 | Valenti et al. |
| 5,246,433 A | 9/1993 | Hasse et al. | 6,306,122 B1 | 10/2001 | Narawa et al. |
| 5,267,933 A | 12/1993 | Precoma | 6,309,336 B1 | 10/2001 | Muessig et al. |
| 5,308,345 A | 5/1994 | Herrin | 6,312,420 B1 | 11/2001 | Sasaki et al. |
| 5,328,438 A | 7/1994 | Crowley | 6,314,333 B1 | 11/2001 | Rajala et al. |
| 5,340,424 A | 8/1994 | Matsushita | 6,315,022 B1 | 11/2001 | Herrin et al. |
| 5,368,893 A | 11/1994 | Sommer et al. | 6,336,921 B1 | 1/2002 | Kato et al. |
| 5,407,513 A | 4/1995 | Hayden et al. | 6,358,350 B1 | 3/2002 | Glaug et al. |
| 5,415,649 A | 5/1995 | Watanabe et al. | 6,369,291 B1 | 4/2002 | Uchimoto et al. |
| 5,421,924 A | 6/1995 | Ziegelhoffer et al. | 6,375,769 B1 | 4/2002 | Quereshi et al. |
| 5,424,025 A | 6/1995 | Hanschen et al. | 6,391,013 B1 | 5/2002 | Suzuki et al. |
| 5,429,576 A | 7/1995 | Doderer-Winkler | 6,416,697 B1 | 7/2002 | Venturino et al. |
| 5,435,802 A | 7/1995 | Kober | 6,443,389 B1 | 9/2002 | Palone |
| 5,449,353 A | 9/1995 | Watanabe et al. | 6,446,795 B1 | 9/2002 | Allen et al. |
| 5,464,401 A | 11/1995 | Hasse et al. | 6,473,669 B2 | 10/2002 | Rajala et al. |
| 5,486,253 A | 1/1996 | Otruba | 6,475,325 B1 | 11/2002 | Parrish et al. |
| 5,494,622 A | 2/1996 | Heath et al. | 6,478,786 B1 | 11/2002 | Gloug et al. |
| 5,531,850 A | 7/1996 | Herrmann | 6,482,278 B1 | 11/2002 | McCabe et al. |
| 5,540,647 A | 7/1996 | Weiermann et al. | 6,494,244 B2 | 12/2002 | Parrish et al. |
| 5,545,275 A | 8/1996 | Herrin et al. | 6,521,320 B2 | 2/2003 | McCabe et al. |
| 5,545,285 A | 8/1996 | Johnson | 6,524,423 B1 | 2/2003 | Hilt et al. |
| 5,552,013 A | 9/1996 | Ehlert et al. | 6,551,228 B1 | 4/2003 | Richards |

| | | | | | | |
|---|---|---|---|---|---|---|
| 6,551,430 B1 | 4/2003 | Glaug et al. | CA | 1190078 | 7/1985 | |
| 6,554,815 B1 | 4/2003 | Umebayashi | CA | 1210744 | 9/1986 | |
| 6,572,520 B2 | 6/2003 | Blumle | CA | 1212132 | 9/1986 | |
| 6,581,517 B1 | 6/2003 | Becker et al. | CA | 1236056 | 5/1988 | |
| 6,596,108 B2 | 7/2003 | McCabe | CA | 1249102 | 1/1989 | |
| 6,605,172 B1 | 8/2003 | Anderson et al. | CA | 1292201 | 11/1991 | |
| 6,605,173 B2 | 8/2003 | Glaug et al. | CA | 1307244 | 9/1992 | |
| 6,637,583 B1 | 10/2003 | Andersson | CA | 1308015 | 9/1992 | |
| 6,648,122 B1 | 11/2003 | Hirsch et al. | CA | 1310342 | 11/1992 | |
| 6,649,010 B2 | 11/2003 | Parrish et al. | CA | 2023816 | 3/1994 | |
| 6,659,150 B1 | 12/2003 | Perkins et al. | CA | 2404154 | 10/2001 | |
| 6,659,991 B2 | 12/2003 | Suckane | CA | 2541194 | 1/2006 | |
| 6,675,552 B2 | 1/2004 | Kunz et al. | CA | 2559517 | 5/2007 | |
| 6,684,925 B2 | 2/2004 | Nagate et al. | DE | 102006047280 | 4/2007 | |
| 6,743,324 B2 | 6/2004 | Hargett et al. | EP | 0044206 | 1/1982 | |
| 6,766,817 B2 | 7/2004 | Dias da Silva | EP | 0048011 | 3/1982 | |
| D497,991 S | 11/2004 | Otsubo et al. | EP | 0089106 | 9/1983 | |
| 6,820,671 B2 | 11/2004 | Calvert | EP | 0304140 | 8/1987 | |
| 6,837,840 B2 | 1/2005 | Yonekawa et al. | EP | 0439897 | 2/1990 | |
| 6,840,616 B2 | 1/2005 | Summers | EP | 0455231 | 11/1991 | |
| 6,852,186 B1 | 2/2005 | Matsuda et al. | EP | 510251 | 10/1992 | |
| 6,875,202 B2 | 4/2005 | Kumasaka et al. | EP | 0652175 | 5/1995 | |
| 6,893,528 B2 | 5/2005 | Middelstadt et al. | EP | 0811473 | 12/1997 | |
| 6,918,404 B2 | 7/2005 | Dias da Silva | EP | 0901780 | 3/1999 | |
| 6,978,486 B2 | 12/2005 | Zhou et al. | EP | 990588 | 4/2000 | |
| 7,066,586 B2 | 6/2006 | Dias da Silva | EP | 1132325 | 9/2001 | |
| 7,077,393 B2 | 7/2006 | Ishida | EP | 1272347 | 1/2003 | |
| 7,172,666 B2 | 2/2007 | Groves et al. | EP | 1571249 | 9/2005 | |
| 7,214,174 B2 | 5/2007 | Allen et al. | EP | 1619008 | 1/2006 | |
| 7,247,219 B2 | 7/2007 | O'Dowd | EP | 1707168 | 4/2006 | |
| 2001/0012813 A1 | 8/2001 | Bluemle | ES | 509706 | 11/1982 | |
| 2001/0017181 A1 | 8/2001 | Otruba et al. | ES | 520559 | 12/1983 | |
| 2001/0042591 A1 * | 11/2001 | Milner et al. ............ 156/252 | ES | 296211 | 12/1987 | |
| 2002/0046802 A1 | 4/2002 | Tachibana et al. | FR | 2255961 | 7/1975 | |
| 2002/0059013 A1 | 5/2002 | Rajala et al. | FR | 0206208 | 12/1986 | |
| 2003/0000620 A1 | 1/2003 | Herrin et al. | FR | 2891811 | 4/2007 | |
| 2003/0015209 A1 | 1/2003 | Gingras et al. | GB | 191101501 | 1/1900 | |
| 2003/0052148 A1 | 3/2003 | Rajala et al. | GB | 439897 | 12/1935 | |
| 2003/0066585 A1 | 4/2003 | McCabe | GB | 856389 | 12/1960 | |
| 2003/0083638 A1 | 5/2003 | Malee | GB | 941073 | 11/1963 | |
| 2003/0084984 A1 | 5/2003 | Glaug et al. | GB | 1096373 | 12/1967 | |
| 2003/0089447 A1 | 5/2003 | Molee et al. | GB | 1126539 | 9/1968 | |
| 2003/0135189 A1 | 7/2003 | Umebayashi | GB | 1346329 | 2/1974 | |
| 2004/0007328 A1 | 1/2004 | Popp et al. | GB | 1412812 | 11/1975 | |
| 2004/0016500 A1 | 1/2004 | Tachibana et al. | GB | 2045298 | 10/1980 | |
| 2004/0112517 A1 | 6/2004 | Groves et al. | GB | 2288316 | 10/1995 | |
| 2004/0164482 A1 | 8/2004 | Edinger | JP | 428364 | 1/1992 | |
| 2005/0000628 A1 | 1/2005 | Norrley | JP | 542180 | 2/1993 | |
| 2005/0196538 A1 | 9/2005 | Sommer et al. | JP | 576566 | 3/1993 | |
| 2005/0230056 A1 | 10/2005 | Meyer et al. | JP | 626160 | 2/1994 | |
| 2005/0230449 A1 | 10/2005 | Meyer et al. | JP | 626161 | 2/1994 | |
| 2005/0233881 A1 | 10/2005 | Meyer | JP | 6197925 | 7/1994 | |
| 2005/0234412 A1 | 10/2005 | Andrews et al. | JP | 100105621 | 2/1998 | |
| 2005/0257881 A1 | 11/2005 | Coose et al. | JP | 10-277091 | 10/1998 | |
| 2005/0275148 A1 | 12/2005 | Beaudoin et al. | SE | 0602047 | 5/2007 | |
| 2006/0021300 A1 | 2/2006 | Tada et al. | WO | WO9747265 | 12/1997 | |
| 2006/0137298 A1 | 6/2006 | Oshita et al. | WO | WO 9747810 | 12/1997 | |
| 2006/0224137 A1 | 10/2006 | McCabe et al. | WO | WO9907319 | 2/1999 | |
| 2006/0265867 A1 | 11/2006 | Schaap | WO | WO9913813 | 3/1999 | |
| 2007/0074953 A1 | 4/2007 | McCabe | WO | WO9965437 | 12/1999 | |
| | | | WO | WO0143682 | 6/2001 | |
| | FOREIGN PATENT DOCUMENTS | | WO | WO0172237 | 10/2001 | |
| CA | 1146129 | 5/1983 | WO | WO2005075163 | 1/2005 | |
| CA | 1153345 | 9/1983 | * cited by examiner | | | |

TRIM REMOVAL SYSTEM

BACKGROUND OF THE INVENTION

The present invention relates to disposable undergarments and, more specifically, to methods and apparatuses for forming disposable undergarments, and particularly to removing unwanted portions of web material such as leg holes, from the undergarment as it is formed.

Generally, disposable undergarments such as pants-type diapers are made up of two nonwoven layers of material with elastic strands of material placed between the two nonwoven layers of material thus creating an elastic web laminate. The layers of material are continuous sheets of material that are eventually cut into individual undergarment lengths. The elastic strands may be arranged and cut so that specific areas of the undergarment are free of elastic tension or forces. An absorbent pad, often contained within an insert or core is then also placed into the pants-type diaper product.

To insure the pants-type diaper retains a proper shape and to hold all of the added layers of the diaper, reinforcing layers and backing materials are normally added to the continuous sheets of material, with the reinforcing layers corresponding to the cut elastic strands of each individual blank. Each of these layers needs to be adhesively joined at some point in the manufacturing process to the elastic web laminate to form the completed undergarment.

Often, void spaces need to be created in the diaper, such as holes cut out of the main web for provided leg holes when the undergarment is ultimately formed. To create the void spaces, the web is ordinarily die cut, with the web severed between a die and an anvil. The portion of the web material that is removed is referred to as a "chip." As the die wears throughout time, the severing of the chip from the web material becomes gradually a duller cut. This complicates the removal of the chip because the severing might not create a continuous cut out chip, with possibly some strands of the web material still coupling the chip with the web. It is desired to lengthen the amount of time and increase the number of chips that a single die can effectively be used for, to reduce the number of die change-outs.

SUMMARY OF THE INVENTION

A system for removing chips from a web is disclosed, the system comprising a rotationally variable speed shoe for receiving a chip, a rotationally constant speed transfer roll for receiving a portion of a web from a die and anvil system, said shoe initially rotating at said constant speed, next slowing in rotational speed to allow said portion of said web to rip away from said chip at a leading rotational edge of said chip, next increasing in rotational speed to allow said chip to rip away from said web at a trailing rotational edge of said chip.

DESCRIPTION OF THE PREFERRED EMBODIMENT

Figure 1:
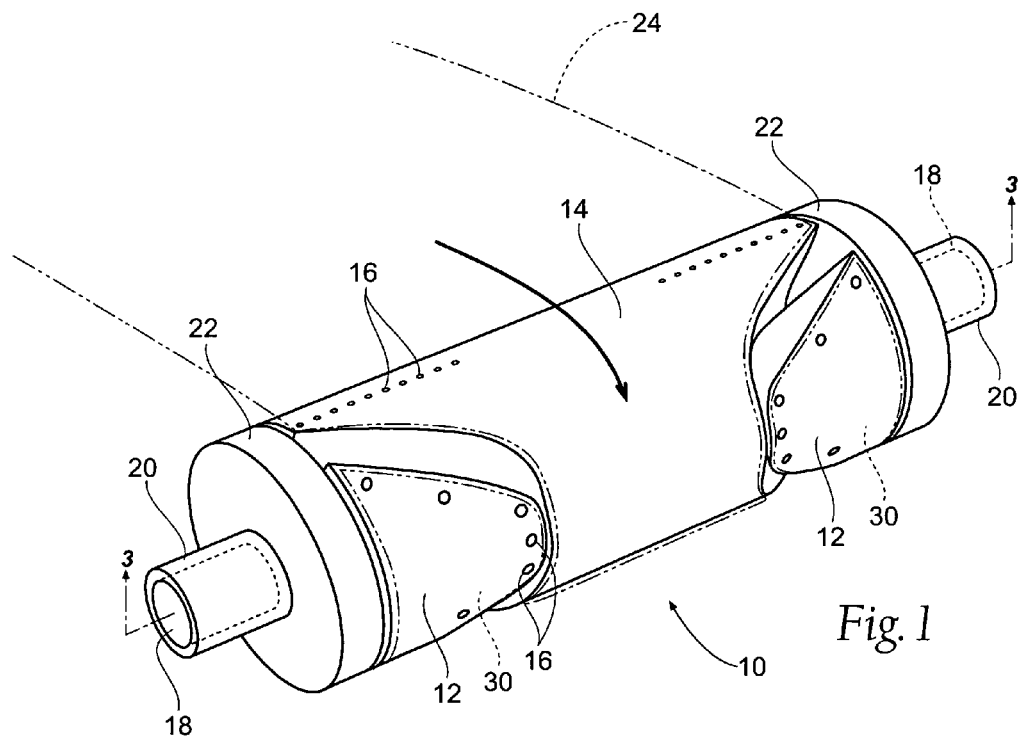
FIG. 1 is a perspective view of a trim shoe of the present invention, with an infeed web, and a chip to be removed therefrom.

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Referring now to FIG. 1a perspective view of a trim removal system 10 of the present invention is shown. An infeed web 24, and a chip or chips 30 to be removed therefrom is shown. A transfer roll 14 and an associated trim shoe or trim shoes 12 are provided to engage the web 24 and chips 30. Preferably, the trim shoes 12 are shaped complimentary with the chips 30. Vacuum ports 16 are provided on the transfer roll 14 and trim shoes 12 for maintaining the web 24 and chips 30 in close contact with the transfer roll 14 and trim shoes 12.

An inner axle 18 and an outer axle 20 are coupled to the transfer roll 14 (or hub 22) and the trim shoes 12, respectively. The inner axle 18 and the outer axle 20 are capable of being operated at different speeds in relation to one another by servo motor (not shown). This difference in speed allows the trim shoes 12 to rotate faster or slower with respect to the transfer roll 14 as desired. In use, as will be described later, this speed differential creates a ripping effect by first pulling the web 24 away from the chip 30 as the transfer roll 14 is rotating faster than the shoe 12, then by pulling the chip 30 away from the web 24 as the shoe 12 is rotating faster than the transfer roll 14.

Figure 2:
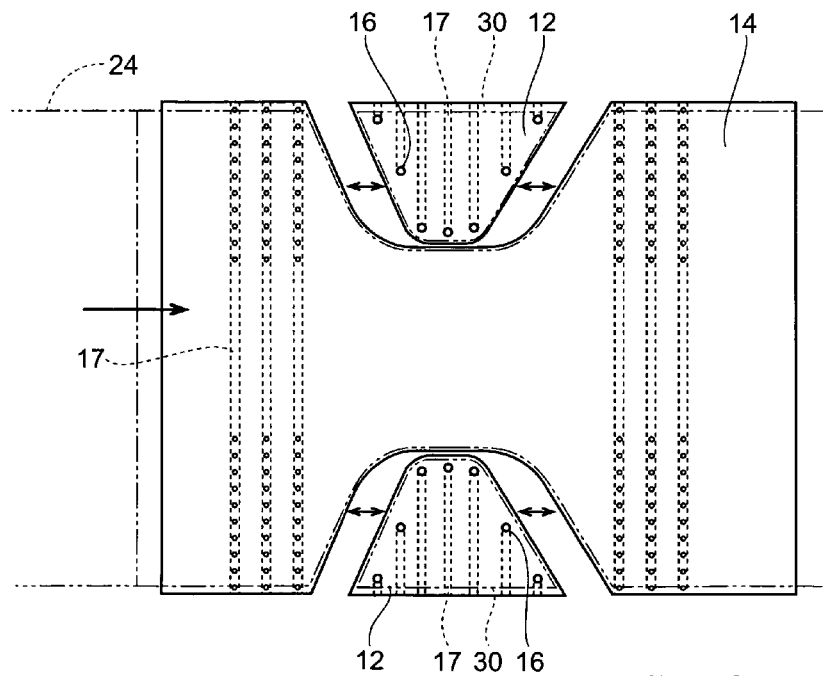
FIG. 2 is a two dimensional representation of the trim shoe of FIG. 1.

Referring now to FIG. 2, a two dimensional representation of the trim shoe 12 and transfer roll 14 of FIG. 1 is shown. As can be seen, vacuum channels 17 communicate with vacuum ports 16 on both the trim shoe 12 and transfer roll 14 to maintain control of the chip 30 and web 24. From this perspective, it can be seen that different rotational speeds of the trim shoe 12 and transfer roll 14 will cause a ripping effect by first pulling the web 24 away from the chip 30 as the transfer roll 14 is rotating faster than the shoe 12, then by pulling the chip 30 away from the web 24 as the shoe 12 is rotating faster than the transfer roll 14.

Figure 3:
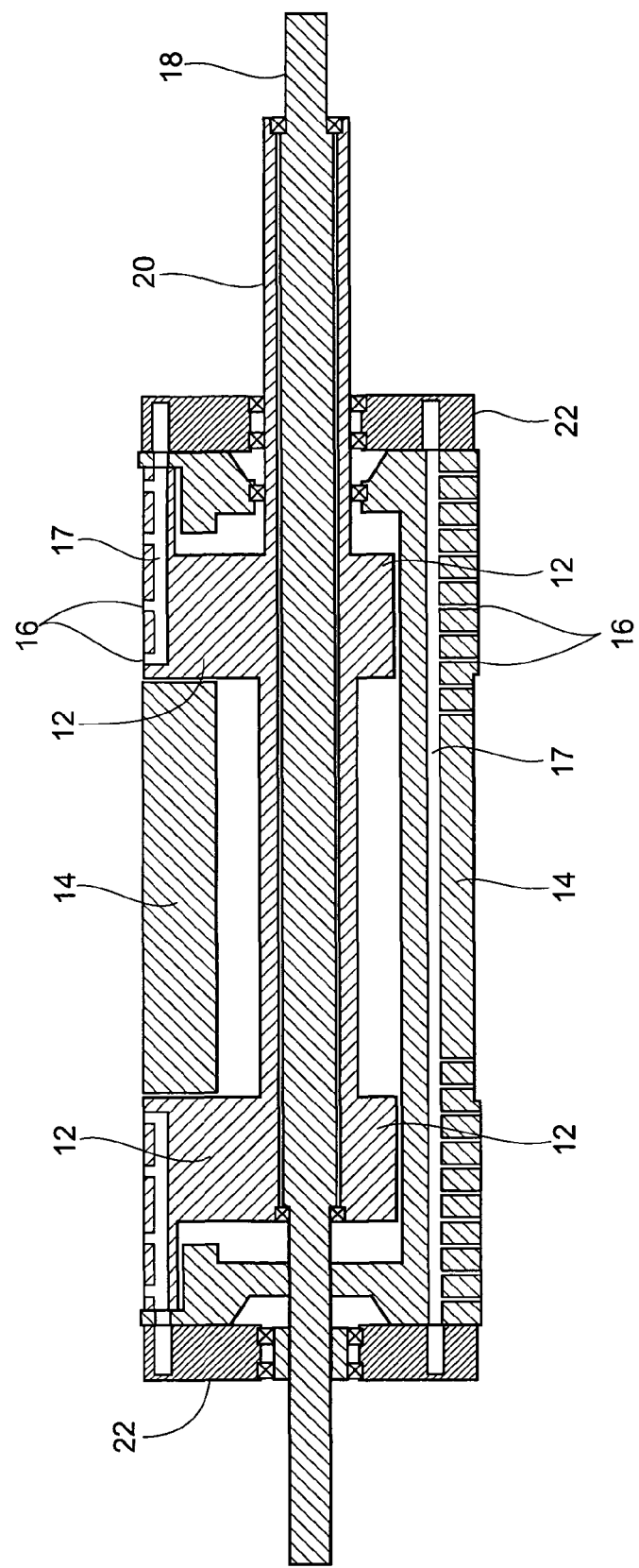
FIG. 3 is a cross sectional view of a trim shoe.

FIG. 3 is a cross sectional view of a trim shoe 12 and transfer roll 14 of the present invention. As can be seen, vacuum is communicated to ports 16 through channels 17, which are coupled to a source of vacuum (not shown). Rotation of the outer axle 20, which is coupled to the shoe 12, causes rotation of the shoe 12. The inner axle 18 is coupled preferably to hub 22 and to transfer roll 14.

Referring now to FIGS. 4-9, a sequence is shown of the trim removal system 10 removing chips 30 and discharging them, and then the system 10 returning to its initial position to remove more chips 30 from the next segment of web 24. FIGS. 10-13 are plan views of the position of the chips 30 relative to the web 24 at the positions associated with FIGS. 4-7 respectively, demonstrating the ripping effects of the present invention.

Figure 4:
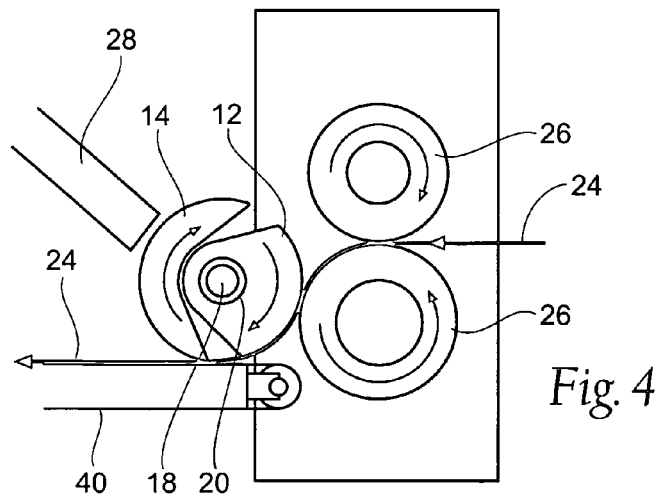
FIG. 4 is a schematic view of a trim shoe receiving an article from a transfer roll in an initial chip engaging position.

Referring now to FIG. 4, a schematic view of the system 10 is shown receiving an infeed web 24. In this figure, die and anvil system 26 is shown rotating to engage the web 24 and cut from it chips 30 (not apparent in this view), as is well known in the art. Unfortunately, the die of the die and anvil system 26 is susceptible to wear and tear and requires replacement once the die dulls to an unacceptable condition.

In this view, the trim shoe 12 can be seen in an initial chip engaging position, aligned to receive the chip 30 of the web 24 onto the shoe 12, which, as described previously, will be urged against the surface of the shoe 12 by vacuum ports 16. The trim shoe 12 will be seen to be rotating about outer axis 20. In this view, a discharge chute 28 is shown for ultimately receiving waste chips 30, and an outfeed conveyor 40 is provided for receiving the web 24 with the chip 30 removed, for further processing and manufacturing steps in the composition of the disposable garments, as desired.

Inner axle 18 is preferably operated at a first continuous speed, rotating hub 22 and transfer roll 14 at a continuous speed, consistent with the infeed speed of the web 24. At this initial chip engaging position shown in FIG. 4, the outer axle 20, and associated shoes 12, are rotated at the same speed as the inner axle 18.

Figure 10:
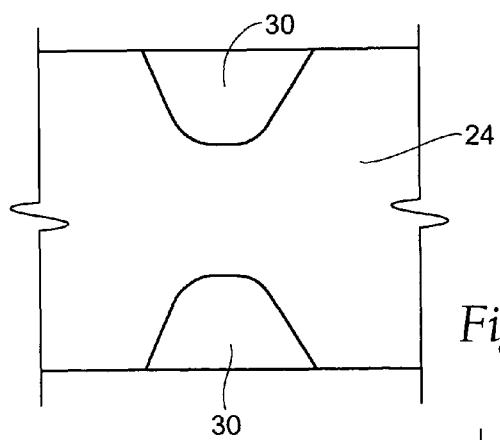
FIGS. 10-13 are plan views of the position of the chip relative to the web, demonstrating the ripping effects of the present invention.

The position of the chip 30 relative to the web 24 is shown in FIG. 10 for the initial chip engaging position. In this position, the anvil and die 26 has created a sever, but the chip 30 and web 24 could remain somewhat coupled depending on the sharpness of the die 26.

Figure 5:
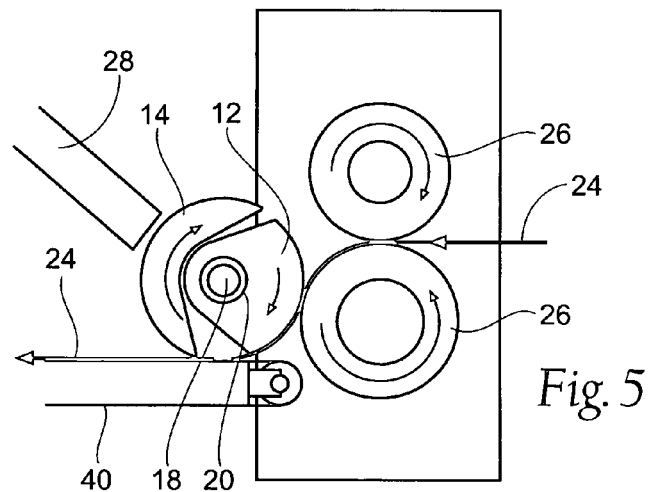
FIG. 5 is a schematic view of the trim shoe separating a first article from a second article.

Referring now to FIG. 5, the outer axle 20, and associated shoes 12, are toggled slower than inner axle 18 to allow the web 24 to be ripped from the chip 30 at the leading edge of the chip 30 in the machine direction. It is apparent in this view that the distance between the trailing edge of the shoes 12 has become closer to the leading edge of the transfer roll 14.

Figure 11:
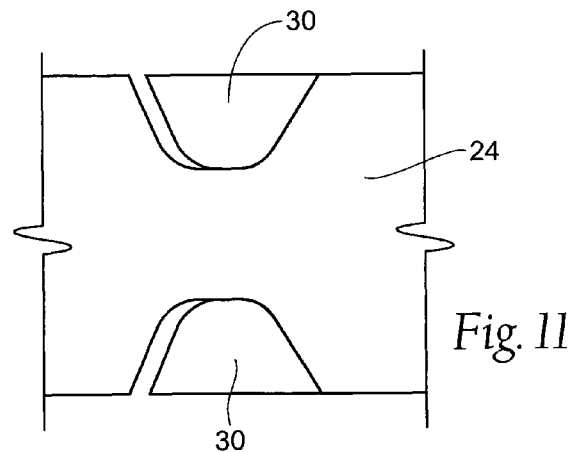

This ripping is caused by the main web 24 being ripped away from the chip 30 at the leading edge of the chip 30 as is shown in associated FIG. 11.

Figure 6:
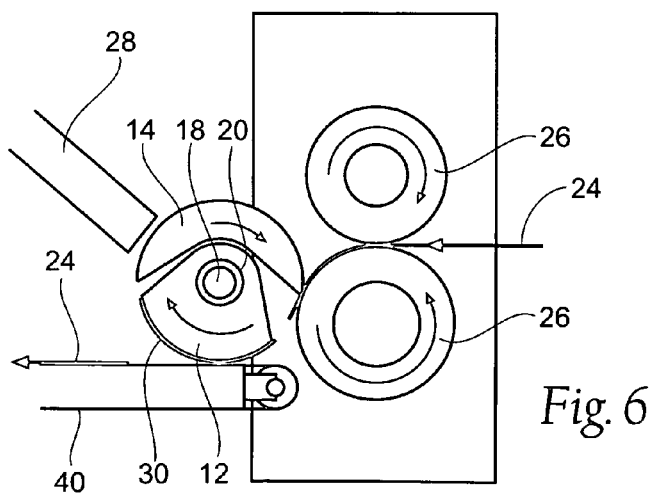
FIG. 6 is a schematic view of the trim shoe separating trim from the first article.
Figure 12:
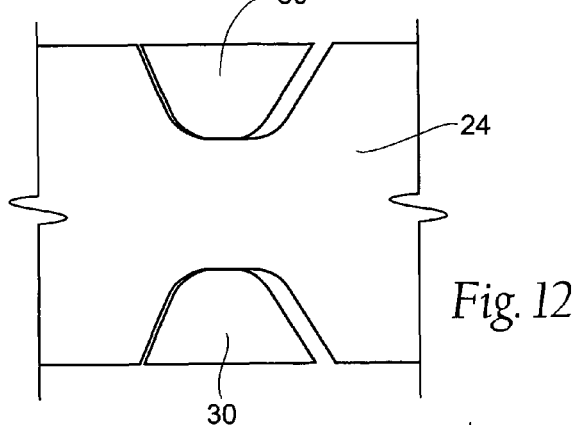

Referring now to FIG. 6, the outer axle 20 is toggled equal to and then faster than the inner axle 18, to allow the chips 30 to rip from the web 24 at the trailing edge of the chips 30 as is shown in associated FIG. 12.

At this point in the process, the chip will be removed from the web 24 by ripping first the main web 24 away from the chip 30 at the leading edge of the chip 30, and next by ripping the trailing edge of the chip 30 from the web 24.

Figure 13:
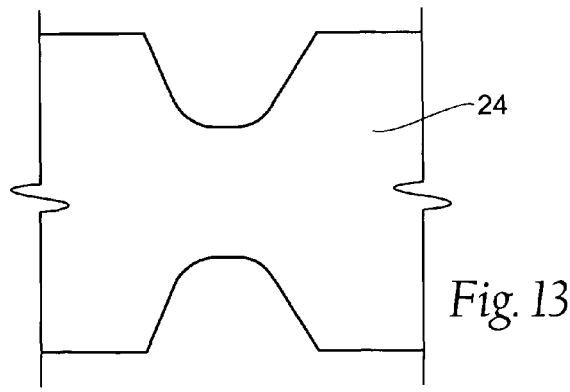

The outfeed conveyor 40 is provided for receiving the web 24 with the chip 30 removed as shown in FIG. 13, for further processing and manufacturing steps in the composition of the disposable garments, as desired. The vacuum of the transfer roll 14 can be turned off at this point to allow for release of the web 24 to the conveyor, for instance in accordance with application Ser. No. 11/141,552, entitled "High Speed Vacuum Porting" which is incorporated herein by reference.

Figure 7:
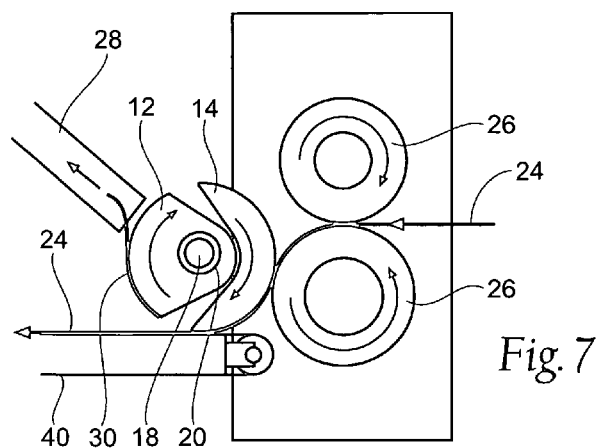
FIG. 7 is a schematic view of the trim shoe discharging the trim.
Figure 8:
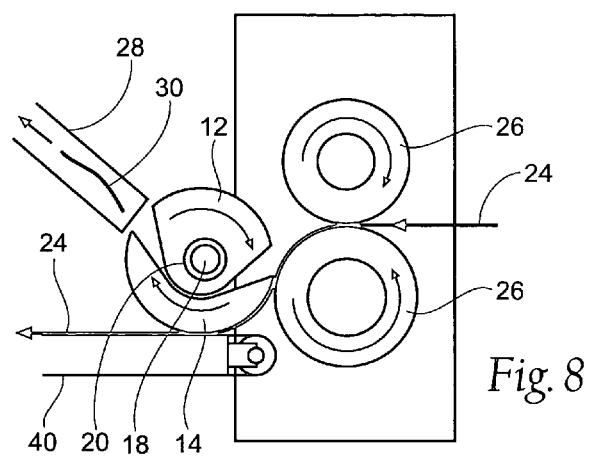
FIG. 8 is a schematic view of the trim shoe returning to its initial chip engaging position.
Figure 9:
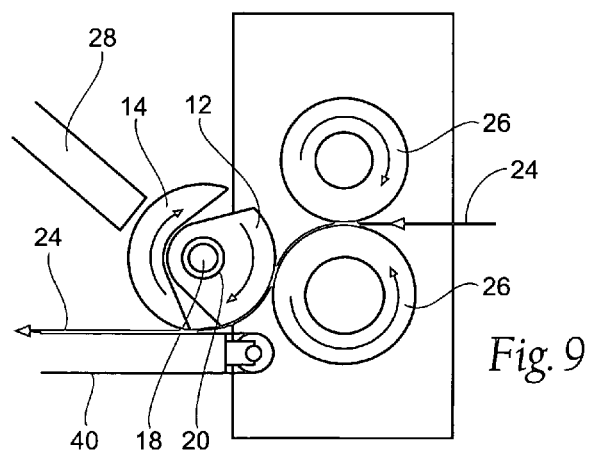
FIG. 9 is a schematic view of the trim shoe returned to its initial chip engaging position.

Referring now to FIG. 7, the chip 30 is discharged into a discharge chute 28, which is preferably vacuum assisted, although other collection means would satisfactorily accomplish the function of collecting waste chips 30.

It is noted that vacuum is allowed to turn off of the shoes 12 to allow the chips 30 to release into the chute 28. Alternatively a vacuum in the chute 28 could simply be provided that is stronger than the vacuum applied to the shoes 12.

The rotational speed of the shoes 12 and outer axle 20, which were first operated at a speed roughly equal to inner axle 18, rotating hub 22 and transfer roll 14, initially decreased, or lagged as is shown by comparing FIG. 4 with FIG. 5.

Next, the rotational speed of the shoes 12 and outer axle 20, increased, or surged relative to the inner axle 18, rotating hub 22 and transfer roll 14.

In order to return to the initial chip engaging position, the rotational speed of the shoes 12 and outer axle 20, must again decrease, or lag relative to the inner axle 18, rotating hub 22 and transfer roll 14. This lag is apparent by comparing FIG. 6 to FIGS. 7, 8 and 9. Finally, in FIG. 9, through one revolution, the system 10 has removed and discharged the chips 30, discharged the web 24 for further processing, and the shoes 12 have been returned to their initial position to remove more chips 30 from the next segment of web 24.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

I claim:

1. A system for removing chips from a web, the system comprising:
   a shoe for receiving a chip, said shoe rotating about an axis driven by a first shaft at a variable speed of revolution, said shoe rotating at a fixed distance from said axis throughout revolution;
   a transfer roll for receiving a portion of a web, said transfer roll rotating about the said axis driven by a second shaft concentric with said first shaft at a constant speed of revolution, said transfer roll rotating at a fixed distance from said axis throughout revolution at said fixed distance from said axis;
   said shoe initially rotating at said constant speed of revolution, next slowing in speed of revolution to allow said portion of said web to rip away from said chip at a leading rotational edge of said chip, next increasing in speed of revolution to allow said chip to rip away from said web at a trailing rotational edge of said chip.

2. The system of claim 1, wherein said shoe is a vacuum shoe.

3. The system of claim 1, wherein said transfer roll is a vacuum transfer roll.

4. The system of claim 1, wherein said chip is discharged by said shoe into a discharge chute.

5. The system of claim 1, wherein said portion of said web is discharged onto a conveyor.

6. The system of claim 1, wherein said shoe and said transfer roll receive said web from an anvil and a die.

7. A system for removing chips from a web, the system comprising:
   a shoe rotating about an axis at a variable speed of revolution for receiving a chip portion of a web;
   a transfer roll rotating about the axis at a constant speed of revolution for receiving a non-chip portion of said web;
   said shoe rotating about an axis at a variable speed of revolution coaxial with said transfer roll rotating about the axis at a constant speed of revolution said shoe being driven rotationally by a first shaft and said transfer roll being driven rotationally by a second shaft that is concentric with the first shaft;
   said transfer roll rotating about the axis at a constant speed of revolution having a void space for receiving said rotationally variable speed shoe and configured to allow said shoe rotating about an axis at a variable speed of revolution to rotate relative to said transfer roll rotating about the axis at a constant speed of revolution;

said shoe initially rotating at said constant speed of revolution, next slowing in speed of revolution to allow said chip portion of said web to rip away from said non-chip portion of said web at a leading rotational edge of said chip, next increasing in speed of revolution to allow said chip portion of said web to rip away from said non-chip portion of said at a trailing rotational edge of said chip;

said shoe rotating about an axis at a variable speed of revolution having a peripheral surface of non-uniform radius.

8. The system of claim 7, wherein said shoe rotating about an axis at a variable speed of revolution is a vacuum shoe.

9. The system of claim 7, wherein said transfer roll is a vacuum transfer roll.

10. The system of claim 7, wherein said chip portion is discharged by said shoe rotating about an axis at a variable speed of revolution into a discharge chute.

11. The system of claim 7, wherein said non-chip portion of said web is discharged onto a conveyor.

12. The system of claim 7, wherein said shoe rotating about an axis at a variable speed of revolution and said transfer roll receive said web from an anvil and a die.

13. The system of claim 7, said peripheral surface of said shoe rotating about an axis at a variable speed of revolution having a first radius and a second radius, said first radius greater than said second radius, thereby forming discontinuities on said peripheral surface.

* * * * *

UNITED STATES PATENT AND TRADEMARK OFFICE
CERTIFICATE OF CORRECTION

| | |
|---|---|
| PATENT NO. | : 7,780,052 B2 |
| APPLICATION NO. | : 11/436274 |
| DATED | : August 24, 2010 |
| INVENTOR(S) | : John A. McCabe |

It is certified that error appears in the above-identified patent and that said Letters Patent is hereby corrected as shown below:

Title Page, Item (74) Attorney; Agent, or Firm– delete the "," after "Ryan" to correctly identify the Attorney Firm as:

--Ryan Kromholz & Manion, S.C.--

(56) References Cited/Other Prior Art insert:

--"Reciprocating Mechanisms, Ingenious Mechanisms for Designers and Inventors", Franklin Jones, Vol. 1--

Column 4, line 61, after "revolution" insert --,--

Signed and Sealed this

Seventh Day of December, 2010

David J. Kappos
*Director of the United States Patent and Trademark Office*